United States Patent [19]

Cherney et al.

[11] Patent Number: 4,533,751

[45] Date of Patent: Aug. 6, 1985

[54] PREPARATION OF 1,3-DIENAMINES FROM MYRCENE AND SUBSTITUTED MYRCENE

[75] Inventors: Leon Cherney; Charles R. Gorman, both of Orange Park; Sean G. Traynor; Carlos G. Cardenas, both of Jacksonville, all of Fla.

[73] Assignee: SCM Corporation, New York, N.Y.

[21] Appl. No.: 310,051

[22] Filed: Oct. 9, 1981

[51] Int. Cl.$^3$ .............................................. C07C 85/18
[52] U.S. Cl. .................................... 564/408; 564/384; 564/485; 544/336
[58] Field of Search ..................... 564/384, 408, 488; 544/336

[56] References Cited

U.S. PATENT DOCUMENTS

| | | | |
|---|---|---|---|
| 2,341,294 | 2/1944 | Rummelsburg | 564/408 X |
| 2,377,682 | 6/1945 | Etzel | 564/408 |
| 2,501,509 | 3/1950 | Gresham et al. | 260/583 |
| 2,518,528 | 8/1950 | Danforth | 564/485 |
| 2,750,417 | 6/1956 | Closson et al. | 564/408 X |
| 4,186,148 | 1/1980 | Murata et al. | 564/485 |

FOREIGN PATENT DOCUMENTS 0410976 1/1976 Japan .
7070776 6/1976 Japan .

OTHER PUBLICATIONS

The Synthesis of Aldehydres from the Reaction of Amines with Butadiene, Apr. 1976, vol. 31, 3713–3718, Zuech, Ernest A., Kleinschmidt, Roger F. and Mahan, John E.

Base-Catalysed Isomerisation of N-(3,7-dimethylocta-2,6-dienyl)dialkylamine to N-(3,7-dimethylocta-1,3-dienyl)dialkylamine: Dihydrocitral from Isoprene, Chem. & Ind., (London), Mar. 5, 1977, p. 202, Tanaka, Minoru and Hata, Go.

The Reaction of Conjugated Olefins with Amines Using Alkali Naphthalene, Chem. & Ind., (London), Mar. 3, 1973, pp. 231–232, Fujita, Tsutomu, Suga, Kyoichi and Watanabe, Shoji.

Butyl Lithium–Catalyzed Stereoselective Telomerization of 1,3-diene-A Novel Synthesis of N,N-Dialkyl-(octa-cis-2,6-dienyl)amine Derivative, Tetrahedron Letters, No. 30, pp. 4009–4012, 1972, Takabe, Kunihiko, Katagiri, Takao and Tanaka, Juntaro, (Printed in Great Britain).

The Reaction of Amines with Conjugated Dienes in the Presence of Alkali Naphthalenide, A New Synthesis of Geranyl Acetate, Aust. J. Chem., 1974, vol. 27, pp. 531–535, Fujita, T., Suga, K., and Watanabe, S.

Noren, J. Org. Chem., vol. 40, No. 7, 1975, pp. 967–968.
Martirosyan et al., CA 59, 6354d, (1963).
Martirosyan et al., CA 62, 11810e, (1965).
Martirosyan et al., CA 63, 14686b, (1965).
Martirosyan et al., CA 68, 86918u, (1968).
Martirosyan et al., CA 68, 38968p, (1968).

*Primary Examiner*—Robert V. Hines
*Attorney, Agent, or Firm*—R. A. Sturges; T. M. Schmitz

[57] ABSTRACT

There is provided a process for the addition of a secondary aliphatic amine to myrcene or an 8-substituted myrcene and isomerization to a dialkyl 1,3-dienamine. The process is liquid phase and employs an excess of the amine relative to myrcene or substituted myrcene. The catalyst is an alkali metal amide anion formed from the amine.

14 Claims, No Drawings

PREPARATION OF 1,3-DIENAMINES FROM MYRCENE AND SUBSTITUTED MYRCENE

This invention relates to a process for making a tertiary dienamine from myrcene or an 8-(alkyl or alkenyl) substituted myrcene. Particularly valuable tertiary dienamines produced in accordance herewith are N-(3,7-dimethylocta-1,3-dienyl)-N,N-dialkylamine, N-(3,7,11,15-tetramethylhexadeca-1,3,14-trienyl)-N,N-dialkyl amine, or N-(3,7,11,15-tetramethylhexadeca-1,3-dienyl)-N,N-dialkyl amine, where the alkyl group is a $C_1$–$C_4$ alkyl group, e.g., methyl.

Tertiary dienamines have utility in that they may be further converted by known means, into various derivatives useful as perfumes and/or flavor chemicals. For example, a particularly valuable reaction intermediate which can be produced from the dienamines produced as described herein is dihydrocitral. (The term "dihydrocitral" as used herein, includes cis and trans isomers of 3,7-dimethyloct-2- and 3-enal). Dihydrocitral is produced by hydrolysis of N-(3,7-dimethylocta-1,3-dienyl)-N,N-diakylamines as reported by Tanaka and Hata, Chem. and Ind. 202 (1977), and can be converted to dihydropseudoionone, a precursor of hexahydropseudoionone, which is a known vitamin E intermediate (B. Stalla-Bourdillon, Ind. Chim. Belg., 35, 13 (1970) and references therein). The 8-substituted 3,7-dimethyloctyl or octenyl myrcene may be converted to phytol or dehydrophytol, respectively also known intermediates to vitamin E. The present invention provides an improved process for making 1,3-dienamines.

BACKGROUND OF THE INVENTION AND PRIOR ART

Previous methods for obtaining this dienamine have generally required two separate steps, one being amination, the second being isomerization. Usually the product of the amination was isolated and followed by catalytic isomerization. In the two-step method, the starting material, for example, myrcene or isoprene, was converted to the corresponding terpenyl amine, e.g., geranylamine (See Fujita et al, Chem. Ind. (London), 231 (1973) or nerylamine, as the case might be. The terpenylamine was recovered and then isomerized in a separate medium using an expensive catalyst. In the case of the nerylamine, for example, the catalyst was an alkali metal 2-aminoethylamide in ethylenediamine (See Tanaka et al, Chem. Ind. (London) 202 (1977)). Alternatively, the prior art utilized a cobalt catalyst with both geranylamine and nerylamine, which gave the dieneamine as a minor by-product. Use of either type of catalyst, however, involved considerable expense and long reaction times to make the desired dienamine.

A method for bringing about the isomerization of an allylic amine to an enamine has been reported (E. A. Zuech, R. F. Kleinschmidt, and J. E. Mahan, J. Org. Chem., 31, 3713 (1966)). The method describes the addition of the primary amine to a butadiene which is followed by the isomerization of the resulting amino-substituted butenyl anion. The mechanism proposed to accomplish the shift of the double bond toward the amino-substituted group is regeneration of the methylamide base. In contact with this strong regenerated base, the 2-butenyl derivative becomes a 1-butenyl compound, reflecting the shift of the double bond one carbon atom closer to the amino-substituted group.

The present process differs from Zuech's proposed route in a number of ways. First, the amine addition compound undergoing isomerization, i.e., shift of the double bond, has at least two double bonds present. Additionally, the shift of the double bond is experienced over a distance of more than one carbon atom and into a conjugate relationship, instead of the one-carbon atom shift contemplated by the Zuech reference. The starting material myrcene or alkyl or alkenyl substituted myrcene is at least a triene. Also the Zuech reference describes double bond migration in a secondary amine system, which contains an acidic proton on nitrogen, and not a tertiary amine system. Finally, the resulting compound in the present process becomes a conjugated diene or a dienamine instead of an enamine. The Zuech reference of course is not a conjugated compound because there is only one double bond present in the product.

Hata et al, Japanese Kokai No. 70707/76 (1976) have shown the reaction of myrcene with a dialkylamine in the presence of a lithium catalyst (liquid phase) to produce geranylamine, not the tertiary dienamine obtained in accordance herewith.

G. T. Martirosyan and others have published several studies relative to reactions of diene hydrocarbons with dimethyl amine (1:1) in the presence of alkali metal. Isoprene was reacted with dimethyl amine in the presence of sodium in benzene to give in high yield (82%) an allylic tertiary amine (CA 59, 6354d (1963)). Dimethyl amine was added to butadiene by introducing the latter into the amine in benzene at 25° C. in the presence of sodium. Again, an allylic tertiary amine was obtained in high yield (81.6%). The amine was present in excess. (CA 62, 11810e (1965)). In another study, the authors passed the dimethyl amine through the conjugated unsaturate (isoprene) in diethyl ether solution in the presence of sodium over 24 hours gave a 70% yield of allylic tertiary amines. (CA 63, 14686b (1965)). Studies were made at 2°–4° C. and 45°–50° C. in reacting isoprene with dimethyl amine in the presence of sodium. It was determined that at higher temperatures, enamine was formed in significant amount. At lower temperatures small amounts of enamine were found. (CA 68, 38968p (1968)). The catalytic activity of Li or K was found to be less effective than Na in the amination of isoprene with dialkyl amine (CA 68, 86981 u (1968)).

Noren, J. Org. Chem. 40, 967 (1975) investigated the effects of various alkali metal catalysts in dialkyl amine additions to isoprene to give 1,4- and 4,1-addition products. Some isomerization was noted at relatively low temperatures (0° to 30° C.).

We have found that the desired tertiary dienamine can be made in a single step, and that the reaction time for the single step can sometimes be shorter than one hour. In addition, the expensive catalysts used to bring about the isomerization in the two-step process have been found to be unnecessary. One less expensive alkalimetal catalyst can be used in the present invention for both amination and isomerization. A one-step process is described wherein the starting polyene and the dialkylamine are both maintained in a liquid phase and in the same vessel for both amination and isomerization. Contrary to much of the prior art, the dialkylamine or secondary amine is utilized in a quantity in excess of stoichiometric relative to the myrcene. Also present is a Group Ia catalyst. The advantage of the present process is clear in view of the use of a less expensive catalyst, as well as ability to make a useful product in a single step without isolation of intermediate or change of medium instead of two or more steps. The product is recoverable by distillation. Yields of the desired product are often in the range of around 40 to 65%. Surprisingly, it is the isolated double bond in the myrcene nucleus that moves into conjugation to form the dienamine. This has not previously been found so far as we have been able to determine.

BRIEF STATEMENT OF THE INVENTION

Briefly stated, therefore, the present invention is in a process for producing an N,N-dialkyl-N-alkyl-1,-3-dienamine by reacting myrcene or an 8-(alkyl or alkenyl) substituted myrcene, with a secondary aliphatic amine in the liquid phase, at a temperature between about $-20°$ C. and 150° C., and in the presence of a catalytic amount of the corresponding alkali metal amide anion of said N,N-dialkylamine for a period of between about 20 minutes to about 50 hours effective to produce a dienamine, the mole ratio of secondary amine to myrcene being greater than 1:1 and up to about 10:1, and recovering the dienamine from the reaction mass.

DETAILED DESCRIPTION AND SPECIFIC EXAMPLES

As indicated above, the present process is productive of useful tertiary terpenyl amines which can be used to form products such as Vitamin E, or flavors or essences for use in perfumes or the like. Basically, the process contemplates adding a secondary aliphatic amine present in molar excess to myrcene or an 8-substituted myrcene in the presence of an amide anion of the diamine. The mode of generating the amide anion catalyst in the reaction mass is immaterial. The catalyst is preferably formed however by adding an alkali metal (sodium, potassium or lithium) or the alkali metal hydride (sodium hydride, potassium hydride or lithium hydride) or the alkali metal alkyl (methyl sodium, methyl potassium or methyl lithium; ethyl sodium, ethyl potassium or ethyl lithium; propyl sodium, propyl potassium or propyl lithium; butyl sodium, butyl potassium or butyl lithium) to the dialkyl amine at a temperature below about 20° C., and especially if using the alkali metal or hydride and then adding the myrcene. The amount of amide anion present initially is generally a catalytic amount, e.g., from 0.1 to 15 mole percent based on the dialkyl amine; more can be used if desired, said amount being controlled by the amount of alkali metal catalytic agent being added and moisture initially present which will consume catalyst until eliminated.

Although myrcene is a naturally occuring terpene hydrocarbon, it may be produced by pyrolysis of beta-pinene. The starting hydrocarbons in the present invention have the general formula:

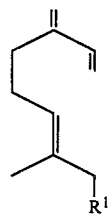

amine, with or without added inert solvent, e.g., an aromatic hydrocarbon, such as benzene, toluene, xylene; or dimethyl sulfoxide or tetrahydrofuran, etc. This is usually best accomplished at 0° C. or below to slow down the reaction to a controllable level. A temperature between 0° C. and $-20°$ C., will be found most satisfactory for this purpose. Thereafter, the myrcene may be added, all at once, or in small portions. The upper temperature need not be controlled and the temperature spontaneously achieved as a result of the exothermic reaction may be the ultimate temperature. Heat may be applied to initiate or accelerate the reaction if desired, although this has not been found to be necessary.

The amount of catalyst has been found to have little effect on the yield and selectivity over the range of about 2 to 10 mole percent based on the weight of polyene hydrocarbon. The amount of catalyst is only significant if the polyene hydrocarbon is wet or contains impurities which can destroy catalyst. In such cases, more alkali metal agent or purification of the starting hydrocarbon is required.

The secondary alkyl or alkylene amine, if normally gaseous as with dimethyl amine, may be introduced as a gas into the reaction vessel. Alternatively, the secondary amine may be dissolved in an inert solvent such as mentioned above, and introduced as a liquid. Alternatively, the secondary amine, if gaseous, may be condensed in the reactor. The temperature of the reactor may then be elevated to reaction temperature.

The time of the reaction varies with the catalyst. Sodium and potassium are quite rapid, accomplishing the addition and isomerization in less than about 5 hours. Lithium has been found to require considerably longer to effect both the addition and isomerization reactions, e.g., at least about 15 hours, to as much as 50 or more hours. If the time of reaction is less than 15 hours, e.g., 2.5 hours at 50° C., the principal product Wherein R'=H, or $C_1$-$C_{10}$ alkyl or alkenyl, e.g., 3,7-dimethyloctyl or an octenyl group. Specific examples include myrcene, 8-methyl myrcene, 8-octyl myrcene, 8-octenyl myrcene and particularly 7,11,15-trimethyl-3-methylene-1,6,14-hexadecatriene (a.k.a. phytatetraene), and 7,11,15-trimethyl-3-methylene-1,6-hexadecadiene (a.k.a. phytatriene).

The secondary amine has the general formula:

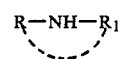

wherein R and $R_1$ are independently selected from $C_1$-$C_5$ alkyl groups, e.g., methyl, ethyl, n-propyl, isopropyl, n-butyl, sec.-butyl, isobutyl, tert.-butyl, amyl, e.g., tert.-amyl, etc., and —R—$R_1$—, e.g., tri-, tetra-, and pentamethylene. Specific examples include dimethyl amine, diethylamine, diisopropyl amine, di-n-butyl amine, di-tert.-butyl amine, methyl ethyl amine, pyrrole, piperidene, indole, pyrrolidine, azetidine, etc. It has been found, that it is the presence of an excess over stoichiometric quantities of dialkyl amine with respect to myrcene that allows the catalyzed addition and isomerization reactions to occur in the same reaction medium to yield a dienamine. The secondary aliphatic amines may, therefore, be dialkyl amines or alkylene cyclic secondary amines, wherein the alkyl or alkylene groups contain 1 to 5 carbon atoms. We prefer $C_1$-$C_2$ di-alkyl amines.

The reaction is conducted in the liquid phase, and if necessary, under sufficient superatmospheric pressure to maintain the reactants in the liquid state in the reactor. Usually temperatures are in the range of from −20° C. to 150° C., and preferably 40° C. to 100° C. In ordinary practice of the invention, the alkali metal amide anion catalyst is formed by any suitable means for producing such catalyst in situ or ex situ and preferably by carefully adding an alkali metal catalyst agent, or an alkali metal hydride catalyst agent or an alkali metal alkyl catalyst agent to the secondary obtained using the lithium catalyst is dialkylgeranyl amine as shown by Hata et al, in Japanese Kokai No. 70707 (1976). Thus, although as we have found all three alkali metals will catalyze the formation of the dienamine with an excess of the secondary amine, lithium is considerably slower. Sodium and potassium catalyzed reactions can be run for the much longer periods, e.g., up to 50 hours or more, but this is both uneconomic and unnecessary.

The reaction may be terminated or quenched by the addition of an alcohol such as ethanol, or with water which destroys the catalyst. Only a very small amount of such terminating agent is required for this purpose. The reaction mass may then be filtered and then distilled to recover the final product.

It has been found that in order to prevent substantial polymerization of myrcene, the secondary amine should be present when the alkali metal catalyst agent and myrcene are brought into contact.

Generally, the alkali metal amide anion catalyst is formed by reacting an alkali metal, an alkali metal hydride, or an alkali metal alkyl with the dialkyl amine with or without an inert solvent at a temperature below 20° C., and preferably from 0° C. to −20° C. A preferred product produced in accordance with this invention is an N,N-dialkyl-N-3,7-dimethyl octa-1,3-dienamine. The alkyl groups are determined by the starting dialkyl amine. This dienamine can be hydrolyzed to form dihydrocitral according to the following reaction:

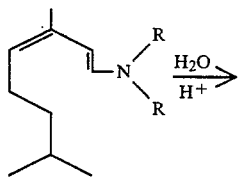

N,N—dialkyl-N—3,7-dimethyl-
octa-1,3-dienamine

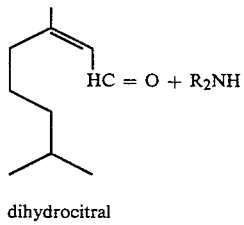

dihydrocitral (See Kumobayashi et al, JACS 100, 3949 (1978)). Dihydrocitral is a Vitamin E precursor.

The following specific examples are for the purpose of illustrating the process of the present invention.

EXAMPLE I 31 milliliters of myrcene (92% pure) and 1 ml of diisopropylamine were charged into a glass pressure reactor of approximately 100 mls capacity. The reactor was equipped with a magnetic stir bar and inlet line connected to a cylinder of dimethylamine. A lithium dispersion in mineral oil weighing 2.2 gms (30% by weight lithium metal, 70% mineral oil) was added and the reactor sealed. The dimethylamine was introduced into the reactor by opening a valve on its storage cylinder. The reactor was immersed in an oil bath at 90° C., and stirred magnetically for 20 hours. The reaction was stopped by the addition of 1 ml of ethanol. The resulting product was washed with water and then analyzed by vapor phase chromatography. The recovered product showed a yield of 53.8% of a product which was identified as N-(3,7-dimethylocta-1,3-dienyl)-N,N-dimethylamine. This product may be easily hydrolyzed to form dihydrocitral. The manner of proceeding from dihydrocitral to Vitamin E is known to those skilled in the art.

EXAMPLE II

In a 2-liter Parr bomb, containing 11.93 gms of 40% sodium/oil dispersion, 375 gms of dimethylamine were condensed into the dispersion. Condensation of the dimethylamine gas was achieved by cooling the reactor to −20° C. The contents of the bomb were then brought to a temperature of 60° C., by immersion in a suitable controlled temperature bath. 682 gms of commercial myrcene containing approximately 90% myrcene and 10% other terpenyl hydrocarbons were added over a 3-hour and 47-minute period of time. During this addition, the temperature in the bomb rose spontaneously to 80° C. and was controlled so as to proceed no higher. At the end of this addition, the contents of the bomb were stirred for an additional hour at 80° C. After the stirring had ceased, a few cc's of water were added to quench the reaction. After cooling to room temperature, the contents of the reactor were filtered. Then, the contents were distilled. The final yield was 384 gms of the N-(3,7-dimethylocta-1,3-dienyl)-N,N-dimethylamine.

Instead of dimethyl amine, diethyl amine, diisopropyl amine, ditert.-butyl amine and the like, may be used to produce equivalent products by the same procedure.

EXAMPLE III 180 gms of myrcene (approximately 90% pure) and 1.45 gms of 40% sodium/oil dispersion were charged into a 400-ml glass pressure bottle. 79 gms of dimethylamine were condensed into the reactants again by cooling to −20° C. The reactants showed a bright red color and were stirred for 115 minutes while the temperature increased from −20° C. to 70° C. The reaction mass was allowed to cool to room temperature (25° C.) and the reaction was quenched with a small amount of water whereupon the color changed from deep red to yellow. The product was next stripped from the reaction at a reduced pressure mixture through a 12-inch Vigreaux column. The final total of the same dienamine produced in the Example I was 112 gms.

EXAMPLE IV 100 gms of commercial myrcene (approximately 90% pure) and 0.90 gms of potassium metal pellets were charged into a 250-ml glass pressure bottle. 34 gms of dimethylamine were condensed into the reactants from dimethylamine gas in a similar manner to the prior example. The contents were stirred for 40 minutes while heating from −20° C. to 94° C. The reactants were allowed to cool to room temperature 25° C. and were quenched with 5 ml of water. The total yield of the desired dienamine was 53.4 gms. after distillation.

EXAMPLE V

Amination-Isomerization 17.9 g. of 7,11,15-trimethyl-3-methylene-1,6,14-hexadecatriene and 40% sodium/oil dispersion (1.2 g) were charged into a small pressure tube containing a magnetic stir bar. The system was sealed and dimethylamine (8.5 g) was condensed into the tube. The pressure tube was then placed in a water bath and, while stirring, the temperature of the water was brought to and held at 75°–80° for 3½ hr. The reaction mixture was cooled and then quenched with water. Filtration resulted in 14.0 g. of material. VPC analysis indicated a peak with the retention time expected for a conjugated dienamine.

Hydrolysis

The organic material (14.0 g) was added to a mixture of glacial acetic acid (11.4 g) and water (103 g). The mixture was stirred at room temperature for 4 hr. At this point, 10% caustic (80 g) was added to the reaction mixture. The resulting organics weighed 10.8 g. VPC analysis was in agreement with hydrolysis of the dienamine and formation of the 8-substituted dihydrocitrals.

What is claimed is:

1. A process for preparing a 1,3-dienamine having the general formula:

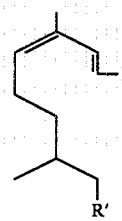

wherein —R and —R$_1$ are independently selected from methyl, ethyl, n-propyl, isopropyl, n-butyl, sec.-butyl, tert.-butyl, amyl, and —R—R$_1$—, and R' is selected from hydrogen and C$_1$–C$_{10}$ alkyl and alkenyl groups, by reacting in the liquid phase a polyene hydrocarbon having the general formula:

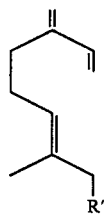

wherein R' is as defined above with a secondary amine selected from dialkyl amines or alkylene cyclic secondary amines wherein the alkyl or alkylene group contains from 1 to 5 carbon atoms, at a temperature in the range of from −20° C. to 150° C. and in the presence of a catalytic amount of the corresponding alkali metal amide ion of said secondary amine for a period of time between about 20 minutes and about 50 hours effective to produce said dienamine, the mole ratio of said secondary amine to said polyene being greater than 1:1 and up to about 10:1, and recovering the dienamine from the reaction mass.

2. A process for producing N,N-dialkyl-N-3,7-dimethyl octa-1,3-dienamine by reacting myrcene in a reaction vessel with a C$_1$–C$_5$ secondary aliphatic amine in the liquid phase at a temperature in the range of from about −20° C. to about 150° C. and in the presence of a catalytic amount of the corresponding alkali metal amide anion of said secondary amine for a period time between about 20 minutes and about 50 hours effective to produce said dienamine, the mole ratio of secondary aliphatic amine to myrcene being greater than 1:1 and up to about 10:1, and recovering the dienamine from the reaction mass.

3. A process as defined in claim 1 wherein the secondary aliphatic amine has the general formula:

R—NH—R$_1$ wherein R and R$_1$ are independently selected from methyl, ethyl, n-propyl, isopropyl, n-butyl, sec.-butyl, tertiary butyl, and amyl.

4. A process as defined in claim 1 wherein the secondary aliphatic amine is dimethyl amine.

5. A process as defined in claim 1 wherein the secondary aliphatic amine is diisopropyl amine.

6. A process as defined in claim 1 wherein the alkali metal amide anion is formed in the reaction vessel from an alkali metal dispersed in a hydrocarbon and the secondary aliphatic amine at a low temperature below about 20° C.

7. A process as defined in claim 1 wherein the alkali metal amide anion is formed in the reaction vessel from an alkali metal hydride and the secondary aliphatic amine.

8. A process as defined in claim 1 wherein the alkali metal amide anion is formed in the reaction vessel from an alkali metal alkyl and the secondary aliphatic amine.

9. A process as defined in claim 6 wherein the alkali metal is sodium metal dispersed in mineral oil and the secondary aliphatic amine is dimethyl amine, and the reaction time is about 5 hours.

10. A process as defined in claim 6 wherein the alkali metal is lithium metal dispersed in mineral oil and the secondary aliphatic amine is diisopropyl amine, and the reaction time is about 20 hours.

11. A process as defined in claim 6 wherein the alkali metal is potassium metal and the secondary aliphatic amine is dimethyl amine.

12. A process as defined in claim 1 wherein the polyene is myrcene.

13. A process as defined in claim 1 wherein the polyene is 7,11,15-trimethyl-3-methylene-1,6,14,-hexadecatriene.

14. A process as defined in claim 1 wherein the polyene is 7,11,15-trimethyl-3-methylene-1,6-hexadecadiene.

* * * * *